United States Patent [19]

Grossman et al.

[11] 3,980,637

[45] Sept. 14, 1976

[54] PRODUCTION OF AMOXICILLIN

[75] Inventors: Joseph H. Grossman; Glenn A. Hardcastle, Jr., both of Syracuse, N.Y.

[73] Assignee: Bristol-Myers Company, New York, N.Y.

[22] Filed: Mar. 17, 1975

[21] Appl. No.: 558,763

[52] U.S. Cl. ............................................. 260/239.1
[51] Int. Cl.² ........................................ C07D 499/68
[58] Field of Search ................................ 260/239.1

[56] References Cited
FOREIGN PATENTS OR APPLICATIONS 1,339,605  12/1973  United Kingdom............ 260/239.1

*Primary Examiner*—Gerald A. Schwartz
*Attorney, Agent, or Firm*—Herbert W. Taylor, Jr.

[57] ABSTRACT

In the production of amoxicillin by acylation of silylated 6-aminopenicillanic acid with the appropriate acid chloride hydrochloride the efficiency of the process and the purity of the product are increased by a new recovery process consisting of isolation from the acylation reaction mixture of solid amoxicillin hydrochloride which is then easily converted to amoxicillin trihydrate.

15 Claims, No Drawings

PRODUCTION OF AMOXICILLIN

BACKGROUND OF THE INVENTION

1. Field of the Invention

The process of the present invention produces an antibacterial agent (amoxicillin) of the class commonly called semi-synthetic penicillins and the subclass characterized by an α-amino group on the acyl sidechain at the 6-position.

2. Description of the Prior Art

The first commercial penicillin having an α-amino group on the 6-acylamido sidechain was ampicillin, which is 6-(D-α-amino-α-phenylacetamido)penicillanic acid (see U.S. Pat. No. 2,985,648).

Amoxicillin is an antibacterial agent used in human therapy and marketed as the trihydrate of the free acid (i.e., the zwitterion). It is described, for example, in *J. Chem. Soc.* (London), pages 1920–1922 (1971) and *Antimicrobial Agents and Chemotherapy* – 1970, pages 407–430 (1971) and in U.S. Pat. No. 3,674,776 (see also U.S. Pat. No. 3,192,198). Its chemical name is 6-[D-α-amino-α-(p-hydroxyphenyl)acetamido]penicillanic acid.

The use of amino acid chloride hydrochlorides to make such penicillins was disclosed in the patent literature, e.g. in U.K. Pat. No. 938,321 and U.K. Pat. No. 959,853 under anhydrous conditions (the latter utilized the protection during acylation of the carboxyl group of the 6-aminopenicillanic acid with a silyl group as was also disclosed in U.K. Pat. No. 1,008,468 and U.S. Pat. No. 3,249,622) and in U.K. Pat. No. 962,719 in cold aqueous acetone. These penicillins are amphoteric amino acids and use was therefore made in their isolation (e.g. as disclosed in U.S. Pat. No. 3,157,640 and U.S. Pat. No. 3,271,389) of certain aliphatic unsymmetrical branched chain secondary amines (often called liquid amine resins) which had previously been used in the isolation of 6-aminopenicillanic acid which is also an amphoteric amino acid (see U.S. Pat. No. 3,008,956). Improved methods of isolating and purifying such penicillins were disclosed, e.g. in U.S. Pat. No. 3,180,862 via β-naphthalene sulfonates and in U.S. Pat. No. 3,198,804 via intermediate isolation and subsequent facile hydrolysis of hetacillin.

The use of a silyl group to protect the carboxyl group of a natural penicillin during chemical cleavage to 6-aminopenicillanic acid was disclosed in U.S. Pat. No. 3,499,909. The use of silylated 6-aminopenicillanic acid during anhydrous acylation with amino acid chloride hydrochlorides was disclosed in numerous patents, e.g. U.S. Pat. No. 3,478,018, U.S. Pat. No. 3,595,855, U.S. Pat. No. 3,654,266, U.S. Pat. No. 3,479,338 and U.S. Pat. No. 3,487,073. Some of these patents also disclose use of liquid amine resins.

U.K. Pat. No. 1,339,605 contains various specific and detailed examples for preparing amoxicillin by the reaction of a silylated derivative of 6-aminopenicillanic acid with a reactive derivative (including the chloride hydrochloride) of D-(-)-α-amino-p-hydroxyphenylacetic acid in which the amino group is protected, thereafter removing the silyl group(s) by hydrolysis or alcoholysis and thereafter, when possible, recovering the amoxicillin, usually as the crystalline trihydrate. Thus crystalline amoxicillin was obtained in Example 1 by isoelectric precipitation from an aqueous solution, e.g. at pH 4.7. Purification was presumably achieved by this example by dissolving the crude product (before isoelectric precipitation) in water at an acidic pH such as 1.0 (e.g. in aqueous hydrochloric acid) in the presence of a water-immiscible organic solvent such as methyl isobutyl ketone (4-methylpentan-2-one). Much the same procedure was used in U.S. Pat. No. 3,674,776.

In U.S. Pat. No. 3,674,776 (Example 10) there is a specific preparation of crystalline amoxicillin hydrochloride trihydrate; a yield of about 74% (1.6 g.) was obtained by dissolving amoxicillin trihydrate (2 g.) in a mixture of 5 ml. water and 2.5 ml. 5 N HCl to give a solution of most of the solid which was quickly filtered and allowed to stand at 5° C.; the crystals were then collected by filtration, washed with a little cold water and dried in an oven at 35°–40° C.

SUMMARY OF THE INVENTION

There is provided by the present invention, in the process for the production of amoxicillin trihydrate which comprises the consecutive steps of:

a. silylating 6-aminopenicillanic acid, preferably with chlorotrimethylsilane (TMCS) or hexamethyldisilazane (HMDS), in an anhydrous solvent, preferably methylene chloride, in the presence of a strong base, preferably a tertiary aliphatic amine and especially triethylamine, b. acylating said silylated 6-aminopenicillanic acid with D-(-)-2-para-hydroxyphenylglycine chloride hydrochloride in the presence of a weak base, preferably dimethylaniline, and its hydrochloride, c. hydrolyzing and neutralizing the product of said acylation to produce amoxicillin trihydrate, and d. recovering the amoxicillin trihydrate, the improvement which comprises mixing the products of the acylation reaction of step (b) with water, and preferably with a volume of water which is one-half the volume of the acylation reaction mixture, at a highly acidic pH, preferably below 2, with the addition of hydrogen chloride if necessary to adjust said pH, and preferably in the presence of large amounts of chloride ion, as exemplifid by the addition of NaCl in an amount by weight of up to 30 percent of the weight of the water used for hydrolysis to form and precipitate solid amoxicillin hydrochloride and then collecting said solid amoxicillin hydrochloride and converting it to amoxicillin trihydrate.

In said process there is further provided by the present invention the process of converting solid amoxicillin hydrochloride to amoxicillin trihydrate by mixing it with, and preferably adding it gradually to, a solution of a liquid, basic high molecular weight aliphatic amine in a water-immiscible organic solvent, preferably methylene chloride or methyl isobutyl ketone, in the presence of a substantial amount of water, preferably about 10 percent of the weight of said organic solvent, and preferably at about 25° C. or below, allowing this mixture to stand for a time sufficient for the completion of the crystallization of amoxicillin trihydrate and finally collecting said amoxicillin trihydrate.

This crystallization of amoxicillin hydrochloride and conversion to amoxicillin trihydrate represents a new and novel method of isolating amoxicillin from anhydrous acylation mix in high yields and excellent quality without the long conversion time associated with our previous procedure in which the crude amoxicillin in the acylation reaction mixture was converted by treatment with acetone over a considerable period of time to the corresponding acetone adduct (see U.K. Pat. No. 1,224,619) which was then isolated and hydrolyzed to amoxicillin. Attempts to acylate with Dane's salt gave acylation yields of only about 55% in our hands as compared to yields of about 80% provided by the process of the present invention. In addition to yield, this process has the advantage over other known processes of high productivity (product weight per reaction volume) and in some cases of higher purity of product.

This process also produces amoxicillin trihydrate of better quality (that is, less color, lower content of DMA and less likely to have deteriorated in potency because less time is required) than the process of quenching acylation mix to produce a very acidic aqueous solution, separating the aqueous phase and then raising its pH to the isoelectric point.

In the process for the production of amoxicillin trihydrate which comprises the consecutive steps of a. silylating 6-aminopenicillanic acid with chlorotrimethylsilane or hexamethyldisilazane in methylene chloride in the presence of triethylamine, b. acylating said silylated 6-aminopenicillanic acid with D-(-)-2-para-hydroxyphenylglycine chloride hydrochloride in the presence of dimethylaniline and its hydrochloride, c. hydrolyzing and neutralizing the product of said acylation to produce amoxicillin trihydrate and d. recovering the amoxicillin trihydrate a preferred embodiment of the present invention is the improvement which comprises mixing the products of the acylation reaction of step b) with a volume of water which is about one-half the volume of the acylation reaction mixture at a pH below 2 and then adding NaCl in an amount by weight of about 20 percent of the weight of the water used for hydrolysis to form and precipitate solid amoxicillin hydrochloride and then collecting said solid amoxicillin hydrochloride and converting it to amoxicillin trihydrate by adding it gradually to a solution of a liquid, basic high molecular weight aliphatic amine in methylene chloride or methyl isobutyl ketone in the presence of an amount of water equal to about 10 percent of the weight of said organic solvent at about 25° C., allowing this mixture to stand for a time sufficient for the completion of the crystallization of amoxicillin trihydrate and finally collecting said amoxicillin trihydrate.

LA-1 resin is a commercially available mixture of secondary amines wherein each secondary amine has the formula

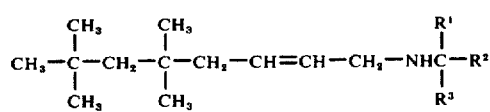

wherein each of $R^1$, $R^2$ and $R^3$ is a monovalent aliphatic hydrocarbon radical and wherein $R^1$, $R^2$ and $R^3$ contain in the aggregate from 11 to 14 carbon atoms. This particular mixture of secondary amines, which is sometimes referred to as "Liquid Amine Mixture No. I", is a clear amber liquid having the following physical characteristics: molecular weight of 351-393; freezing point below −80° C; neutralization equivalent of 380-410; acid binding capacity of 2.5-2.7 meq./gm.; viscosity at 25° C. of 72 cps.; specific gravity at 25° C. of 0.84; % (volume) distilled at 10 mm. below 160° C.

= 5% maximum; 50% (volume) distillation point at 10 mm. = 210° C.

Amberlite LA-1 is thus an aliphatic unsymmetrical unsaturated amine having at least 12 carbon atoms in one group and a molecular weight of at least 185. Amberlite LA-2 is a similar amine except that it is straight chained and saturated. LA-2 has the formula

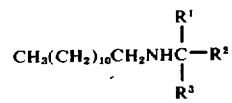

wherein each of $R^1$, $R^2$ and $R^3$ is a monovalent aliphatic hydrocarbon radical and wherein $R^1$, $R^2$ and $R^3$ contain in the aggregate from 11 to 14 carbon atoms. This particular mixture of secondary amines, which is sometimes referred to as "Liquid Amine Mixture No. II", is a clear amber liquid having the following physical characteristics: viscosity at 25° C. of 70 cps., specific gravity at 20° C. of 0.826; refractive index at 25° C. of 1.4554; distillation range at 10 mm., up to 170° C. - 0.5%, 170°-220° C. - 3%, 220-230° C. - 90% and above 230° C. - 6.5%.

The members of this class are thus aliphatic amines of the group consisting of straight chain, branched chain, saturated, unsaturated, symmetrical, unsymmetrical secondary amines having at least 12 carbon atoms in one group and a molecular weight of at least 185.

The preferred members of this class have the formula

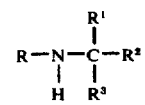

wherein R is an aliphatic group having from 10 to 14 carbon atoms and $R^1$, $R^2$ and $R^3$ are each alkyl groups having in the aggregate a total of from 11 to 14 carbon atoms.

The members of this class can be used in place of the LA-1 of the example below and are referred to herein as liquid, basic high molecular weight aliphatic amines.

The following example is given in illustration of, but not in limitation of, the present invention. All temperatures are in degrees Centigrade. Methyl isobutyl ketone is represented as MIBK.

DESCRIPTION OF THE PREFERRED EMBODIMENTS

Example: Amoxicillin via Anhydrous Acylation - Isolation via a Hydrochloride Intermediate

I. EQUATIONS

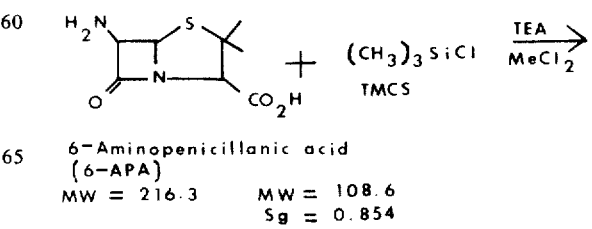

6-Aminopenicillanic acid (6-APA)
MW = 216.3    MW = 108.6
              Sg = 0.854

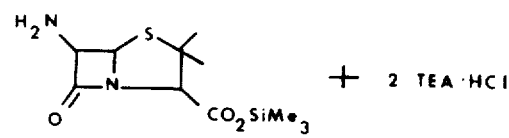

↓

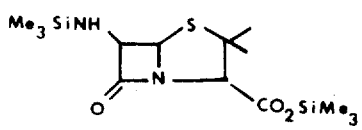

Silyl 6-APA*

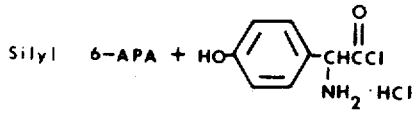

D-(−)-2-p-hydroxyphenylglycine
chloride hydrochloride
MW = 222

Silylated amoxicillin hydrochloride
MW = 473.9

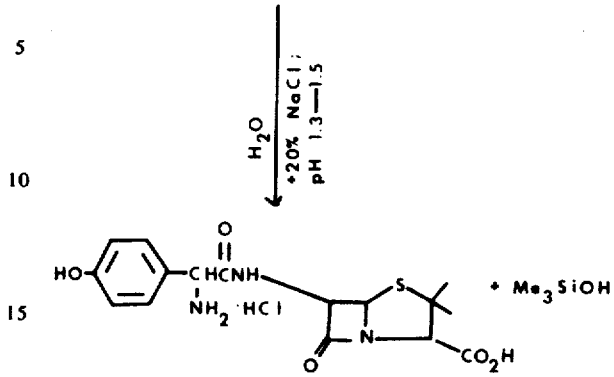

Amoxicillin hydrochloride
MW = 401.5

↓ MILA

Amoxicillin trihydrate
MW = 419.4

\* It is believed that 2 moles TMCS makes a mixture of silylated compounds with 100% silylation at carboxyl group and about 60% silylation on the amino group.

II. MATERIALS

| | Weight & Volume Required | Moles | Mole Ratio |
|---|---|---|---|
| 6-APA | 1 kgW (KF = 0.02%) | 4.62 | 1.0 |
| MeCl$_2$ (methylene chloride) | 20 l. (sieve-dried) as needed [1] | — | — |
| TEA (triethylamine) | 1.29 l. [2] | 9.26 | 2. |
| TMCS (trimethylchlorosilane) | 1.17 l. | 9.26 | 2. |
| DMA (N,N-dimethylaniline) | 0.696 l. | 5.48 | 1.2 |
| DMA.HCl | 1.49 kgW of solution [3] | 2.82 | 0.61 |
| D-(−)-2-p-hydroxyphenylglycine chloride hydrochloride | 1.26 kgW of 82% pure | 4.63 | 1.0 |
| Water | 12.5 l. or 50% of measured acylation mix volume — also as needed | — | — |
| Sodium Chloride | 2.5 kgW or 20% of the water volume | — | — |
| 6 N HCl | As needed | — | — |
| 15% LA-1 Resin/MIBK (MILA) | 37.5 l. of LA-1 in MIBK (5.625 l. LA-1 in 37.5 l. total volume) | — | — |
| Filter-Aid (diatomaceous earth) | 500 g. of acid wash (or low Fe Content) | — | — |

Notes: [1] Molecular sieve drying removes water and methanol from the MeCl$_2$.
[2] This procedure calls for 2 moles of TEA and TMCS. with the variations in input APA and MeCl$_2$ (recovered vs. new) this level has been shown to give more consistent results. This procedure is also effective at 1.6 moles TEA and TMCS.

|  | Weight & Volume Required | Moles | Mole Ratio |
|---|---|---|---|
| (3) 30% wt/wt DMA.HCl solution, 1.25 g/cc. | | | |

III. SAFETY

Trimethylchlorosilane (TMCS) - Flammable. Highly reactive with moisture to give off HCl.

D-(-)-2-p-hydroxyphenylglycine chloride hydrochloride - Highly reactive with moisture to give off HCl.

TEA. DMA are both two well-known toxic chemicals which should be handled with the usual great care.

Amoxicillin hydrochloride - Toxicity and allergenic properties are unknown. Handle this with the same care as all penicillins.

Rest of chemicals are well-known and should be handled with normal precautions.

IV. PROCEDURE

1. To 20 l. of $MeCl_2$ at 25° C., add 1 kgW of 6-APA. Add 1.29 l. of TEA at 25° to 28° C., agitate 30 min. - 6-APA should nearly dissolve.

2. At 20° to 25° C. add 1.17 l. of TMCS. Allow the temperature to rise 25° to 27° C. Add the TMCS over a 5–10 min. period. Hold 60 min. at 25° C.

3. Cool to 0° to 5° C. Add 0.696 l. of DMA and 1.49 kgW of DMA.HCl solution. Begin acylation immediately.

4. Sprinkle in 1.26 kgW D-(-)-2-p-hydroxyphenylglycine chloride hydrochloride in three aliquots as follows:

Add ⅓ of the D-(-)-2-p-hydroxyphenylglycine chloride hydrochloride (430 g.) at 0° to 5° C. over a 5 min. period. Allow the acylation mix to cool back to about 3° C. Add a second aliquot of D-(-)-2-p-hydroxyphenylglycine chloride hydrochloride rapidly. Allow the temperature to rise to about 5° C. Hold 10 min. while cooling back to <5° C. Add the final amount of D-(-)-2-p-hydroxyphenylglycine chloride hydrochloride (430 g.), keeping the temperature below 10° C. — if possible, 5° C.[(4)] Age the acylation mix at 0 to 5°C. (3° C. preferably) for 2 hr.

4. It is helpful to use 32° F brine at this step.

5. The acylation mix must be polished. In the laboratory this is best accomplished as follows:

a. To the cold acylation mix add 500 g. of low iron content filter-aid (in the laboratory acid-washed filter-aid was used — this contains 36 ppm Fe and a KF of 0.05%). Do not allow "wet" filter-aid (higher KF than 0.05%) to come in contact with the acylation mix.

b. Hold approximately 5 min. and polish filter rapidly into 12.5 l. of well-agitated ice cold $H_2O$ (or 50% of the measured acylation mix volume). Wash the filter cake with methylene chloride.

c. Mix for 5 to 10 minutes.

6. The amoxicillin hydrochloride is crystallized at 0–5° C. as follows:[(5)]

a. Sprinkle in about ⅛ of the total 2.5 kgW NaCl (about 300 g.) into the 0° to 5° C. hydrolysis mix. Seed with 10 g. of amoxicillinn hydrochloride if possible — if not, add a little more salt (about 100 g.). Hold for about 5 to 10 minutes; should observe a heavy bed of amoxicillin hydrochloride crystals — if not, add a little more salt.

b. Once a heavy bed of crystals is established (this should not take more than 10 min. — the hydrolysis mix is not too stable), add another ⅛ portion of salt. Total added is 25%. Hold 5 minutes.

c. Now add the remaining 75% total salt (about 1.25 kgW) over 10 to 15 min. The entire operation should not take more than 30 min., however it is important that a good amoxicillin hydrochloride slurry be established at a low salt concentration. This leads to low DMA content in the final amoxicillin trihydrate.

d. After all the salt is added, make sure the pH of the slurry is at 1.3 to 1.5, adding 6 N HCl if necessary. Agitate 30 min. at 0°–5° C.

5. A second technique is available for precipitating the hydrochloride salt. The acylation mix is polished into 40% volume water. After a 10 min. hold, 10% volume salt solution (30 g./100 ml.) is slowly dripped in until a heavy crystal slurry is formed. The remaining salt (approximately 1.75 kgW) is added slowly as a solid. This should give maximum precipitation at a low salt concentration.

Filter, wash with $MeCl_2$ and 2.5 to 4 l. of ice cold, clear, saturated (35 g. salt/100 ml.) sodium chloride solution. Pull dry enough under vacuum so that the product wet cake can be safely handled.

7. At 25° C. convert the amoxicillin hydrochloride to amoxicillin trihydrate by adding it to a mixture of 37.5 l. of 15% LA-1 in MIBK[(6)] and 3.75 l. of $H_2O$. Sprinkle the cake into the MILA with good agitation. Sprinkle at a slow rate, allowing the cake to disperse and convert to $3H_2O$.

6. LA-1 in methylene chloride (MeLA) can be used in place of MILA. MILA may give slightly lower DMA than MeLA.

8. Hold 2 to 3 hr. at 25° C., collect by filtration, wash thoroughly with MIBK and then with 2 l. of cold $H_2O$. Cake may be flashed with acetone. Dry at 40° C. for 14 to 16 hr.

The yield is usually 1.50–1.59 kgW of 98% pure amoxicillin trihydrate (Bio) from 98.7% pure 6-APA; 77–82% activity yield. The DMA content is usually < 10 ppm.

The following represents recent laboratory data on the isolation of amoxicillin hydrochloride from anhydrous acylation mix. The amoxicillin hydrochloride is then converted to amoxicillin trihydrate by slurrying in LA-1 resin (dissolved in $MeCl_2$ or MIBK) and 10% water. The process represents a very efficient method of preparing good quality, low DMA (< 15 ppm, usually < 10 ppm) amoxicillin trihydrate. It has the advantage of excellent yields and high productivity over other known methods of preparing amoxicillin.

SUMMARY

1. A procedure for the preparation of amoxicillin trihydrate via anhydrous acylation and isolation via the amoxicillin hydrochloride intermediate is set forth above. 2. Lab experiments gave 77 to 82% activity yields to amoxicillin trihydrate from 6-APA. A normal isolation leaves 6 to 9% activity assayed as amoxicillin in the salt mother liquor; 2 to 3% amoxicillin in the LA-1 mother liquor and approximately 3% unreacted 6-APA.

3. The major problem has been maintaining a DMA content of less than 15 ppm in the final amoxicillin trihydrate. This was accomplished most consistently by:

a. Mixing acylation mix with a half volume water, followed by slow addition of solid NaCl (20% of the water volume by weight).

b. Slow addition of amoxicillin hydrochloride cake to the LA-1 dissolved in MIBK or MeCl$_2$ (MILA or MeLA).

4. When normal production grade 6-APA is used for an acylation, a polish filtration of the anhydrous acylation mix must be used.

5. It has not been possible in this laboratory to obtain standard amoxicillin yields without the addition of at least 0.5 mole of the hydrochloride of a weak base (DMA) prior to acylation. Quinoline can be substituted for DMA if quinoline hydrochloride is used in the same ratio as DMA hydrochloride. One acylation with isoquinoline was unsuccessful.

6. The best acylation yields from 6-APA to amoxicillin continue to be at a 1 mole D-(-)-2-p-hydroxyphenylglycine chloride hydrochloride level. In one comparison, 0.95 mole D-(-)-2-p-hydroxyphenylglycine chloride hydrochloride gave a 3% better yield to amoxicillin based on the acid chloride than 1 mole.

Laboratory Data

Listed in Table I are the results obtained when amoxicillin cake (from amoxicillin+6 N HCl) is slurried in salt solution over a pH range of 0.5 to 1.75. This shows that amoxicillin.HCl has very little solubility in 20 to 30% NaCl solution. It is also quite stable at pH 1.0 to 1.5. When the hydrochloride is precipitated from acylation mix, 6 to 9% amoxicillin is assayed in the salt solution. These losses are higher than expected from the solubility table and may be due partly to the formation of para-methoxy-ampicillin.HCl from D-(-)-2-p-hydroxyphenylglycine chloride hydrochloride containing para-methoxy-phenylglycyl chloride.HCl.

Previously, amoxicillin hydrochloride to amoxicillin trihydrate experiments from lab and plant acylation mixes only gave 65 to 70% yields. This was due to quenching the mixes in 10 to 20% by volume of saturated salt solutions at pH 0.5. These low yields must have been caused by severe decomposition in the highly concentrated low pH solution. Table II shows that excellent yields can be obtained when the water volume is increased to 50% of the acylation mix volume. Comparison of 15 to 30% salt over a pH range of 0.3 to 1.5 (adjusted after the HCl cake precipitated) showed that 25 to 30% gave a product with unacceptable (> 15 ppm) DMA content. A level of 20% at pH range 1.3 to 1.5 gave the best results in the lab. These experiments were done with recrystallized 6-APA; no polish filtration step required.

Plant grade 6-APA usually contains insoluble dark color bodies which must be removed. Table III shows that polish filtration of hydrolysis mixes (pH 1.5) through a Dicalite-coated filter resulted in slightly lower yields. It has been demonstrated that amoxicillin hydrochloride will precipitate from a stirred hydrolysis mix when seeded or stirred too long. The safest method is to polish the anhydrous acylation mix. The use of filter-aid as admix in the lab (only experience is 50% by weight, filteraid to APA) resulted in yields of 76 to 79% amoxicillin trihydrate. Product colors were higher than expected but generally within specifications. The use of acidwashed filter-aid did not result in improved yields or color.

Table IV lists experiments in which the amoxicillin hydrochloride was precipitated by various techniques with NaCl used as a solid and solution. It was theorized that the use of a salt solution as a precipitant might result in crystallization of the HCl'd salt at low NaCl concentrations. This should have led to amoxicillin trihydrate products of consistently low DMA content but it did not prove to be true in the experiments tried. The most successful results came when 20% salt was sprinkled into the hydrolysis mix over 30 min.

Table V gives some idea of the stability of the amoxicillin hydrochloride slurry over a 16 hr. period. At 0° to 5° C. the maximum yield loss was only 3%. Crystallization of the amoxicillin hydrochloride slurry at 25° C. resulted in a lower weight precipitated and the remaining product was found in the mother liquor. However, no attempt was made to precipitate the product cold and then warm to 25° C. The advantage might be to precipitate a product with half the DMA content of the cold slurried product.

Table VI lists some experiments on the amoxicillin hydrochloride to amoxicillin trihydrate conversion slurries. The data indicate that 15% LA-1 in MIBK or MeCl$_2$ (containing 10% H$_2$O) works well. Acetone washing did not seem to influence the DMA content. Use of other solvents such as butanol or heptane did not reduce DMA contents (product is quite soluble in wet butanol system).

In Table VII the use of the hydrochloride of a weak base (DMA, quinoline or isoquinoline) was investigated. Omitting the weak base.HCl resulted in lower yields when compared to the standard procedure. It is also interesting to note that the amount of TEA.TMCS influences the offset in yield. In most of the experiments (not all) the residual APA content was higher when the weak base.HCl was omitted. It is also interesting to note that the base content of amoxicillin trihydrate from quinoline acylation is much higher than for DMA acylations. No attempt was made to do direct crystallizations - all products were prepared via the HCl intermediate.

Table VIII represents the brief experiences at 0.9, 0.95 and 1.0 mole D-(-)-2-p-hydroxyphenylglycine chloride hydrochloride. As indicated, 1 mole D-(-)-2-p-hydroxyphenylglycine chloride hydrochloride gave the best APA yields but 0.95 mole gave a better D-(-)-2-p-hydroxyphenylglycine chloride hydrochloride yield. In all acylations there is approximately a 5 to 10% hole in the material balance. Thus, addition of 10% extra D-(-)-2-p-hydroxyphenylglycine chloride hydrochloride does not result in a corresponding increase in amoxicillin trihydrate yield.

TABLE I

Solubility Data
Amoxicillin hydrochloride vs pH & % NaCl
Bio Potency, mcg./ml.

| pH | H$_2$O | 5% NaCl | 10% NaCl | 20% NaCl | 30% NaCl |
|---|---|---|---|---|---|
| 0.5 | 10600 | 5600 | 5700 | 2130 | 1260 |
| 1.0 | 32000 | 8500 | 4560 | 1980 | 1500 |
| 1.25 | 53500 | 9100 | 4680 | 1770 | 1130 |
| 1.5 | 53500 | 10000 | 5650 | 2070 | 1130 |
| 1.75 | 55000 | 12300 | 6000 | 2100 | 1180 |

TABLE II pH. Salt Concentration vs. Yield and DMA Content of Amoxicillin Trihydrate

| Experiment | | pH | % Scm* | Bio mcg./mg. | % Act. Yld. | Klett | DMA ppm | Ash | % Cl- |
|---|---|---|---|---|---|---|---|---|---|
| Add aliquots of acylation mix | Ⓐ | 1.3 | 82.3 | 857 | 81 | 48 | 31 | 0.2 | 0.34 |
| to 50% H₂O - Hold 10 min. - | Ⓑ | 1.0 | 81 | 844 | 79 | 49 | 46 | 0.1 | .16 |
| Add 30% salt - Seed - | Ⓒ | 0.3 | 81.2 | 862 | 80.4 | 43 | 32 | 0.1 | 0.14 |
| Convert 15% MeLA | Ⓓ | as is (1.4–1.5) | 81.2 | 849 | 79.2 | 50 | 41 | 0.1 | 0.26 |
| Add aliquots of acylation mix to 50% H₂O | as is | (1.4–1.5) | | | | | | | |
| Ⓐ Hold 10 min, add 15% NaCl - 1 shot | | as is (1.4–1.5) | 79.0 | 866 | 78.6 | 44 | 9 | <0.1 | 0.15 |
| Ⓑ Hold 10 min, add 20% NaCl- 1 shot | | as is (1.4–1.5) | 83.0 | 868 | 82.6 | 45 | 7 | <0.1 | 0.09 |
| Ⓒ Hold 10 min, add 25% NaCl - 1 shot | | as is (1.4–1.5) | 84.0 | 866 | 83.5 | 65 | 18 | <0.1 | 0.22 |

*% Scm refers to stoichiometric yield, that is, percent yield assuming pure reagents and pure product.

TABLE III

Polish Filtering Acylation Mix or Hydrolysis Mix Prior to Amoxicillin Hydrochloride Ppt. Step

| | | | | Analyses on Amoxicillin Trihydrate Produced | | | | | |
|---|---|---|---|---|---|---|---|---|---|
| % H₂O Hyd. Step | % NaCl | Polish Step | Experiment | % Scm | Bio mcg/mg | % Act. Yd. of amoxicillin trihydrate | DMA | Ash | Klett |
| 60 | 20 - slow | Hyd. Mix | Add H₂O Polish - Process | 77.5 | 866 | 77.4 | 8 | <.1 | 55 |
| '' | '' | '' | Sep. phases - Cryst. H₂O—MeCl₂ | 76.9 | 866 | 76.9 | 7 | <.1 | 39 |
| 50 | '' | '' | Add H₂O - Polish - Process | 75.5 | 874 | 75.8 | 27.6⁽¹⁾ | 0.1 | 57 |
| '' | '' | Acyl. Mix | use dry F.A.⁽²⁾ as admix | 79 | 870 | 79.3 | 11 | 0.1 | 82 |
| '' | '' | '' | 5-μ funnel - N₂ bag-No F.A. | 77.6 | 875 | 78 | 12.8 | <0.1 | 74 |
| '' | 24 - slow | '' | Add mix - Regular F.A.⁽²⁾ | 76 | 836 | 73.9 | 15 | <0.1 | 93 |
| '' | '' | '' | Add mix - Wet F.A.⁽²⁾ | 76.8 | 858 | 76.7 | 18 | <0.1 | 94 |
| '' | '' | '' | Add mix - Dry F.A.⁽²⁾ | 77.4 | 883 | 78.4 | — | — | — |
| 60 | 20 | '' | Dry F.A. - Use as precoated filter | 79.7 | 836 | 77.5 | 10 | <0.1 | 80 |
| '' | '' | Hyd. Mix | Polish as above | 76.4 | 849 | 73.5 | <0.5 | <0.1 | 59 |
| 50 | '' | Acyl. Mix | Use acid-washed F.A.⁽²⁾ as admix | 77.7 | 840 | 75.9 | 10 | <0.1 | 119 |

Notes:
⁽¹⁾Only one sample sent in for DMA assay - on some samples variability can be as high as 100%.
⁽²⁾"Dry F.A." = acetone-washed and dried filter-aid. "Regular F.A." = filter-aid as it comes from Production. "Wet F.A." = filter-aid that has been slurried in water and air-dried. "Acid-Washed F.A." = washed in HCl - neutralized - acetone-washed and dried.

TABLE IV

Amoxicillin Trihydrate DMA Content etc. vs. Technique of Amoxicillin Hydrochloride Precipitation

| % Vol. H₂O | % Total Added Salt | pH | Experiment | % Scm | Bio mcg/mg | % Act. Yd. | DMA ppm | Comments |
|---|---|---|---|---|---|---|---|---|
| 50 | 20 | 1.4–1.5 | Control - Add salt - 1 shot | 83 | 868 | 82.6 | 7 | Recryst. APA - No polish filtration step |
| '' | '' | '' | Add acyl. mix to salt - H₂O | 75.8 | 849 | 73.5 | 8 | '' |
| '' | '' | '' | Add salt - 1 shot | 80.5 | 874 | 80.4 | 18 | '' |
| '' | '' | '' | Add salt - 2 shots over 10 min. | 79.5 | 887 | 79.5 | 7 | '' |
| 75 | '' | '' | Add salt - 1 shot | 79.4 | 870 | 79.4 | 7 | '' |
| 100 | '' | '' | Add salt - 1 shot | 78.4 | 891 | 78.4 | 7 | '' |
| '' | '' | '' | Dilute acyl. mix w/100% MeCl₂ | 78 | 870 | 78 | 6 | '' |
| 30 | '' | '' | SOP - slow addition | 80.5 | 858 | 79.3 | 13 | '' |
| 15 | '' | '' | SOP - slow addition | 77.6 | 849 | 75.6 | 9 | '' |
| 20 | '' | 1.3 | Add salt solution to hyd. mix slowly | 78.4 | 879 | 78.4 | 10 | '' |
| 30 | '' | '' | Add salt solution to hyd. mix slowly | 76 | 870 | 76 | 8 | '' |
| 20 | '' | '' | Add salt solution to hyd. mix rapidly | 78.8 | 870 | 78.8 | 15 | '' |
| 50 | '' | '' | Add solid salt slowly | 77.7 | 840 | 75.9 | 10 | Polish filtration step- Plant APA |
| 20 | '' | '' | Use 30% vol. salt solution + solid | 76.9 | 849 | 76.5 | 18 | '' |
| 40 | '' | '' | Use 10% vol. salt solution + solid | 79 | 840 | 77.2 | 13 | '' |

TABLE V

Stability of Amoxicillin Hydrochloride Slurry at pH 1.4
1.7 (Unadjusted) - 25% NaCl Solution

| Sample | Temp. Held | Time | Amoxicillin.HCl 100 ml. | % of Control | mcg. in ML |
|---|---|---|---|---|---|
| 1 | 0.5°C. | 0.5 hr. | 7.63 | 100 | 370,000 |
| 2 | " | 1 hr. | 7.95 | 104 | 360,000 |
| 3 | " | 1.5 hr. | 7.64 | 100 | 370,000 |
| 4 | " | 2 hr. | 7.85 | 103 | 320,000 |
| 5 | " | 3 hr. | 7.50 | 98 | 360,000 |
| 6 | " | 16 hr. | 7.37 | 96.6 | 360,000 |
| 7 | 25° C. | 2 hr. | 6.4 | 84 | 610,000 |

DMA content of amoxicillin hydrochloride samples prepared at 0 to 5°C. was 6390 ppm.
DMA content of sample number 7 was 3300 ppm.
The dried amoxicillin hydrochloride cake in sample number 2 was converted to amoxicillin trihydrate,
82% yield, Bio 862, DMA 33.

TABLE VI

Conversion Step

| % $H_2O$ | NaCl | Conversion Mix | Experiment | % Scm | Bio mcg/mg | % Act. Yd. | DMA ppm |
|---|---|---|---|---|---|---|---|
| 50 | 20 | pH 5, 15% MeLA | As in the Example above | 79.5 | 849 | 77.5 | 6 |
| " | " | pH 5, 20% MeLA | As in the Example above | 78.8 | 858 | 77.6 | 8 |
| " | " | pH 5, 15% MILA | As in the Example above | 79.4 | 862 | 78.6 | 4 |
| " | " | pH 5, 15% MeLA | Slurry in acetone | 78.7 | 853 | 77.1 | 9 |
| " | " | 15% MeLA, pH unadjusted | Heavy MeCl₂ was on amoxicillin hydrochloride cake prior to conversion | 78.5 | 853 | 76.9 | 17 |
| " | " | 15% MeLA, pH unadjusted | Add conversion mix to the HCl cake | 81.3 | 78.9 | 10 | |
| " | " | 15% MeLA, pH unadjusted | Acetone wash amoxicillin trihydrate in filter funnel | 81.3 | 831 | 77.6 | 12 |
| " | " | 15% MeLA, pH unadjusted | Control | 79.9 | 888 | 79.9 | 4 |
| " | " | 15% MILA, pH unadjusted | As in the Example above | 77.9 | 879 | 77.9 | 5 |
| " | " | 20% BuLA, pH unadjusted | As in the Example above | 58.7 | 875 | 58.7 | 18 |
| " | " | 15% LA-1 in heptane, pH unadjusted | As in the Example above | 78.4 | 853 | 76.8 | 12 |

TABLE VII

Use of DMA - Quinoline - Isoquinoline
Importance of the Base.HCl Addition & Relation to Ester Make-up

| Ester | | Base | | Base.HCl | | % $H_2O$ | % Salt | % Scm | Bio mcg/mg | % Act. Yd | Base ppm | Comments |
|---|---|---|---|---|---|---|---|---|---|---|---|---|
| 2.0 | moles TMCS-TEA | 1.2 | DMA | 0.6 | DMA.HCl | 50 | 24 | 82.5 | 874 | 82.5 | 6 | Recryst. 6-APA input |
| " | " | " | " | 0.61 | " | " | 20 | 83 | 868 | 82.6 | 7 | " |
| 1.6 | " | " | " | 0 | " | " | " | 74 | 874 | 74 | 6 | " |
| 2.0 | " | " | Quin | 0 | Quin.HCl | " | 24 | 68.1 | 849 | 66.4 | 82 | " |
| 1.6 | " | " | " | 0 | " | " | " | 77 | 858 | 75.9 | 75 | " |
| " | " | 1.0 | " | 0 | " | " | 20 | 73.2 | 883 | 73.2 | 33 | " |
| 2.0 | " | " | " | 0.125 | " | " | 24 | 73.4 | 870 | 73.4 | 24 | " |
| " | " | " | " | 0.25 | " | " | " | 75.0 | 866 | 75 | 24 | " |
| " | " | " | " | 0.5 | " | " | " | 80.4 | 871 | 80.4 | 17 | " |
| " | " | " | " | 0.6 | " | " | " | 80.6 | 866 | 80.1 | 13 | " |
| " | " | " | " | 0.75 | " | " | " | 78.5 | 862 | 77.7 | 24 | " |
| " | " | 1.2 | Iso-quin | 0.6 | Isoquin. HCl | " | " | 55 | 848 | 53.5 | NA | " |

TABLE VIII

D-(-)-2-p-hydroxyphenylglycine chloride hydrochloride - Amoxicillin trihydrate Yield Via
Amoxicillin hydrochloride Process

| Mole D-(-)-2-p-hydroxyphenyl-glycine chloride hydrochloride | % APA Scm | Bio mcg/mg | % Act. Yd. | % D-(-)-2-p-hydroxyphenylglycine chloride hydrochloride Act. Yd. |
|---|---|---|---|---|
| 1.0 | 77.7 | 840 | 78.2 | 78.2 |
| 0.9 | 70.9 | 845 | 69.7 | 77.4 |
| 0.95 | 76.3 | 875 | 76.3 | 81.4 |

We claim:

1. In the process for the production of amoxicillin trihydrate which comprises the consecutive steps of a. silylating 6-aminopenicillanic acid in an anhydrous solvent in the presence of a strong base,
b. acylating said silylated 6-aminopenicillanic acid with D-(-)-2-para-hydroxyphenylglycine chloride hydrochloride in the presence of a weak base and its hydrochloride,
c. hydrolyzing and neutralizing the product of said acylation to produce amoxicillin trihydrate and
d. recovering the amoxicillin trihydrate the improvement which comprises mixing the products of the acylation reaction of step (b) with water at a highly acidic pH below 2 to form and precipitate solid amoxicillin hydrochloride and then collecting said solid amoxicillin hydrochloride and converting it to amoxicillin trihydrate.

2. In a process of claim 1 the process of converting solid amoxicillin hydrochloride to amoxicillin trihydrate by mixing it with a solution of a liquid, basic high molecular weight aliphatic amine in a water-immiscible organic solvent in the presence of a substantial amount of water, allowing this mixture to stand for a time sufficient for the completion of the crystallization of amoxicillin trihydrate and finally collecting said amoxicillin trihydrate.

3. In the process of claim 1 the process of converting solid amoxicillin hydrochloride to amoxicillin trihydrate by adding it gradually to a solution of a liquid, basic high molecular weight aliphatic amine in a water-immiscible organic solvent in the presence of a substantial amount of water at about 25°C., allowing this mixture to stand for a time sufficient for the completion of the crystallization of amoxicillin trihydrate and finally collecting said amoxicillin trihydrate.

4. In the process of claim 1 the process of converting solid amoxicillin hydrochloride to amoxicillin trihydrate by adding it gradually to a solution of a liquid, basic high molecular weight aliphatic amine in methylene chloride or methyl isobutyl ketone in the presence of a substantial amount of water, allowing this mixture to stand for a time sufficient for the completion of the crystallization of amoxicillin trihydrate and finally collecting said amoxicillin trihydrate.

5. In the process of claim 1 the process of converting solid amoxicillin hydrochloride to amoxicillin trihydrate by adding it gradually to a solution of a liquid, basic high molecular weight aliphatic amine in methylene chloride or methyl isobutyl ketone in the presence of an amount of water equal to about 10 percent of the weight of said organic solvent at about 25° C., allowing this mixture to stand for a time sufficient for the completion of the crystallization of amoxicillin trihydrate and finally collecting said amoxicillin trihydrate.

6. In the process of claim 1 for the production of amoxicillin trihydrate which comprises the consecutive steps of
a. silylating 6-aminopenicillanic acid in an anhydrous solvent in the presence of a strong base,
b. acylating said silylated 6-aminopenicillanic acid with D-(-)-2-para-hydroxyphenylglycine chloride hydrochloride in the presence of a weak base and its hydrochloride,
c. hydrolyzing and neutralizing the product of said acylation to produce amoxicillin trihydrate and
d. recovering the amoxicillin trihydrate the improvement which comprises mixing the products of the acylation reaction of step (b) with water at a highly acidic pH below 2 in the presence of large amounts of chloride ion to form and precipitate solid amoxicillin hydrochloride and then collecting said solid amoxicillin hydrochloride and converting it to amoxicillin trihydrate.

7. In the process of claim 1 for the production of amoxicillin trihydrate which comprises the consecutive steps of
a. silylating 6-aminopenicillanic acid in an anhydrous solvent in the presence of a strong base,
b. acylating said silylated 6-aminopenicillanic acid with D-(-)-2-para-hydroxyphenylglycine chloride hydrochloride in the presence of a weak base and its hydrochloride,
c. hydrolyzing and neutralizing the product of said acylation to produce amoxicillin thihydrate and
d. recovering the amoxicillin trihydrate the improvement which comprises mixing the products of the acylation reaction of step (b) with water at a pH below 2 and in the presence of NaCl in an amount by weight of up to 30 percent of the weight of the water used for hydrolysis to form and precipitate solid amoxicilin hydrochloride and then collecting said solid amoxicillin hydrochloride and converting it to amoxicillin trihydrate.

8. In the process of claim 1 for the production of amoxicillin trihydrate which comprises the consecutive steps of
a. silylating 6-aminopenicillanic acid in an anhydrous solvent in the presence of a strong base,
b. acylating said silylated 6-aminopenicillanic acid with D-(-)-2-para-hydroxyphenylglycine chloride hydrochloride in the presence of a weak base and its hydrochloride,
c. hydrolyzing and neutralizing the product of said acylation to produce amoxicillin trihydrate and
d. recovering the amoxicillin trihydrate the improvement which comprises mixing the products of the acylation reaction of step (b) with a volume of water which is about one-half the volume of the acylation reaction mixture at a pH below 2 and in the presence of NaCl in an amount by weight of up to 25 percent of the weight of the water used for hydrolysis to form and precipitate solid amoxicillin hydrochloride and then collecting said solid amoxicillin hydrochloride and converting it to amoxicillin trihydrate.

9. In the process for the production of amoxicillin trihydrate which comprises the consecutive steps of
a. silylating 6-aminopenicillanic acid in an anhydrous solvent in the presence of a strong base,
b. acylating said silylated 6-aminopenicillanic acid with D-(-)-2-para-hydroxyphenylglycine chloride hydrochloride in the presence of a weak base and its hydrochloride,
c. hydrolyzing and neutralizing the product of said acylation to produce amoxicillin trihydrate and
d. recovering the amoxicillin trihydrate the improvement which comprises mixing the products of the acylation reaction of step b) with a volume of water which is about one-half the volume of the acylation reaction mixture at a pH below 2 and then adding NaCl in an amount by weight of about 20 percent of the weight of the water used for hydrolysis to form and precipitate solid amoxicillin hydrochloride and then collecting said solid amoxicillin hydrochloride and converting it to amoxicillin trihydrate.

10. In the process of claim 9 the process of converting solid amoxicillin hydrochloride to amoxicillin trihydrate by mixing it with a solution of a liquid, basic high molecular weight aliphatic amine in a water-immiscible organic solvent in the presence of a substantial amount of water, allowing this mixture to stand for a time sufficient for the completion of the crystallization of amoxicillin trihydrate and finally collecting said amoxicillin trihydrate.

11. In the process of claim 9 the process of converting solid amoxicillin hydrochloride to amoxicillin trihydrate by adding it gradually to a solution of a liquid, basic high molecular weight aliphatic amine in a water-immiscible organic solvent in the presence of a substantial amount of water at about 25° C., allowing this mixture to stand for a time sufficient for the completion of the crystallization of amoxicillin trihydrate and finally collecting said amoxicillin trihydrate.

12. In the process of claim 9 the process of converting solid amoxicillin hydrochloride to amoxicillin trihydrate by adding it gradually to a solution of a liquid, basic high molecular weight aliphatic amine in methylene chloride or methyl isobutyl ketone in the presence of a substantial amount of water, allowing this mixture to stand for a time sufficient for the completion of the crystallization of amoxicillin trihydrate and finally collecting said amoxicillin trihydrate.

13. In the process of claim 9 the process of converting solid amoxicillin hydrochloride to amoxicillin trihydrate by adding it gradually to a solution of a liquid, basic high molecular weight aliphatic amine in methylene chloride or methyl isobutyl ketone in the presence of an amount of water equal to about 10 percent of the weight of said organic solvent at about 25° C., allowing this mixture to stand for a time sufficient for the completion of the crystallization of amoxicillin trihydrate and finally collecting said amoxicillin trihydrate.

14. In the process for the production of amoxicillin trihydrate which comprises the consecutive steps of
   a. silylating 6-aminopenicillanic acid with chlorotrimethylsilane or hexamethyldisilazane in methylene chloride in the presence of triethylamine,
   b. by acylating said silylated 6-aminopenicillanic acid with D-(-)-2-para-hydroxyphenylglycine chloride hydrochloride in the presence of dimethylaniline and its hydrochloride,
   c. hydrolyzing and neutralizing the product of said acylation to produce amoxicillin trihydrate and
   d. recovering the amoxicillin trihydrate the improvement of which comprises mixing the products of the acylation reaction of step b) with a volume of water which is about one-half the volume of the acylation reaction mixture at a pH below 2 and then adding NaCl in an amount by weight of about 20 percent of the weight of the water used for hydrolysis to form and precipitate solid amoxicillin hydrochloride and then collecting said solid amoxicillin hydrochloride and converting it to amoxicillin trihydrate.

15. In the process of claim 14 the process of converting solid amoxicillin hydrochloride to amoxicillin trihydrate by adding it gradually to a solution of a liquid, basic high molecular weight aliphatic amine in methylene chloride or methyl isobutyl ketone in the presence of an amount of water equal to about 10 percent of the weight of said organic solvent at about 25° C., allowing this mixture to stand for a time sufficient for the completion of the crystallization of amoxicillin trihydrate and finally collecting said amoxicillin trihydrate.

* * * * *